United States Patent [19]

Bar-Shalom et al.

[11] Patent Number: 5,240,710
[45] Date of Patent: Aug. 31, 1993

[54] METHOD OF TREATING CONDITIONS OF TEETH AND THEIR SUPPORTING TISSUE WITH SUCRALFATE

[75] Inventors: Daniel K. Bar-Shalom, Kokkedal; Niels Bukh, Strandvejen 122, KX-2900 Hellerup; Jesper Hamburger, Rungsted Kyst, all of Denmark

[73] Assignees: Niels Bukh, Hellerup; Tandlaegeselskabet Jesper Hamberger ApS, Niva, both of Denmark; a part interest

[21] Appl. No.: 939,969

[22] Filed: Sep. 4, 1992

Related U.S. Application Data

[63] Continuation of Ser. No. 375,006, Aug. 4, 1989, abandoned.

[30] Foreign Application Priority Data

Feb. 26, 1988 [DK] Denmark .............................. 1024/88
Sep. 9, 1988 [DK] Denmark .............................. 5055/88

[51] Int. Cl.$^5$ .......................... A61K 7/20; A61K 7/16; A61K 31/735
[52] U.S. Cl. .................................... 424/422; 424/401; 424/405; 424/56
[58] Field of Search ....................... 464/53, 54, 56, 422

[56] References Cited

U.S. PATENT DOCUMENTS

| | | | |
|---|---|---|---|
| 3,432,489 | 3/1969 | Yoshihiro et al. | 536/118 |
| 3,538,230 | 11/1970 | Pader et al. | 424/50 |
| 4,359,458 | 11/1982 | Nair et al. | 514/54 |
| 4,599,363 | 10/1986 | Woo | 152/268 |
| 4,618,488 | 10/1986 | Maeyama et al. | 424/49 |
| 4,632,826 | 12/1986 | Ploger et al. | 424/52 |
| 4,701,319 | 10/1987 | Woo | 424/52 |
| 4,702,905 | 10/1987 | Mitchell et al. | 70/279 |
| 4,716,034 | 12/1987 | Schelm | 424/49 |
| 4,721,614 | 1/1988 | Winston et al. | 424/52 |
| 4,772,470 | 9/1988 | Inoue et al. | 424/435 |
| 4,912,093 | 3/1990 | Michaeli | 514/53 |

FOREIGN PATENT DOCUMENTS

| | | |
|---|---|---|
| 97625 | 1/1984 | European Pat. Off. . |
| 136100 | 4/1985 | European Pat. Off. . |
| 161816 | 4/1985 | European Pat. Off. . |
| 107209 | 9/1986 | European Pat. Off. . |
| 230023 | 7/1987 | European Pat. Off. . |
| 245855 | 11/1987 | European Pat. Off. . |
| 280077 | 2/1988 | European Pat. Off. . |
| 133880 | 12/1988 | European Pat. Off. . |
| 192640 | 3/1989 | European Pat. Off. . |
| 3430809 | 8/1984 | Fed. Rep. of Germany . |
| 8404453 | 11/1984 | PCT Int'l Appl. . |
| 8900047 | 1/1989 | PCT Int'l Appl. . |
| 409036 | 4/1974 | Sweden . |

OTHER PUBLICATIONS

Loe, et al., J. of Periodontology 36:177-187; 1965.
Loesche, et al., Caries Research 9:139-155, 1975.

(List continued on next page.)

Primary Examiner—Thurman K. Page
Assistant Examiner—Neil S. Levy
Attorney, Agent, or Firm—Iver P. Cooper

[57] ABSTRACT

The use of a sulphated saccharide or a salt or a complex thereof as an ingredient in a topical preparation for the prophylaxis or treatment of diseases or conditions of the tooth or tooth-supporting tissue, in particular for the prophylaxis or treatment of inflammatory and plaque-related conditions, a method of preventing or treating such diseases or conditions by topically applying the sulphated saccharide or salt or complex thereof, and a topical preparation containing the sulphated saccharide or salt or complex thereof for the prophylaxis or treatment of such diseases or conditions. The sulphated saccharide is especially a polysulphated or persulphated saccharide. e.g. sucralfate (sucrose octakis(hydrogen sulphate) aluminum complex) or a sodium and/or potassium salt of sucrose octakis(hydrogen sulphate). The preparation may be in the form of a solution, suspension, salve, paste, powder, gel, cream, dental fixative, periodontal implant, chewing gum, chewable tablet, effervescent tablet or lozenge.

48 Claims, No Drawings

OTHER PUBLICATIONS

Bartold and Page, J. Oral Path. 15: 367-374, 1986.
Last, et al., Archs Oral Biol. 30(3):275-281, 1985.
Embery & Hogg, Proc., Strasbourg, Ed. R. M. Frank & S. A. Leach, pp. 185-194, Oct. 1981.
"Sucralfate: Nonulcer Uses", The American Journal of Gastroenterology, 80(3):206-209, 1985.
Ferraro & Mattern, Drug Intell. Clin. Pharm. 18: 153, 1984.
Loe, J. Periodont. 38: 38-44, 1967.
The Gingival Index, Plaque Retention Index Systems
Chemical Abstracts, vol. 101, 1984 abstract No. 168321h, Lab. Pathophysiol., Nat.'l Cancer Inst., Bethesda, MD 20205.
Translation of Greek Search Report.
Patent Abstract of Japan; vol. 13, No. 61 (C-567) [3409], Feb. 10, 1989; & JP-A-63 253 018 (Sunstar Inc.) Oct. 20, 1988.
Patent Abstract of Japan; vol. 14, No. 143 (C-703)[4086], Mar. 19, 1990; & JP-a-2 015 020 (Uemosiyaku Oyo Kenkyusho K.K.) Jan. 18, 1990.
Patent Abstract of Japan; vol. 12, No. 56 (C-477)[2903], Feb. 19, 1988; & JP-A-62 201 825 (Lion Corp.) Sep. 5, 1987.

METHOD OF TREATING CONDITIONS OF TEETH AND THEIR SUPPORTING TISSUE WITH SUCRALFATE

This application is a continuation, of application Ser. No. 07/375,006, filed Aug. 4, 1989 now abandoned.

FIELD OF INVENTION

The present invention relates to the use of sulphated saccharides for the treatment of conditions of teeth and tooth-supporting tissue.

TECHNICAL BACKGROUND

Both gingivitis and periodontitis are inflammatory diseases caused by plaque formation on the teeth. Chronic periodontitis often leads to destruction of the tissues supporting the teeth. Plaque can be defined as a soft bacteria-containing coating on the surface of a tooth. When a tooth is not clean, plaque formation will commence and this will lead to gingivitis in the gingival area.

The inflammation of the gingiva leads to the formation of the gingival sulcus, and a gingival pocket is formed. Clear evidence that plaque is responsible for gingivitis was derived from the induction of experimental gingivitis (H. Loe et al., *J. Periodontology* 36: 177–187, 1965). Starting from a state of clinical gingival health, all participants developed gingivitis within 10 to 21 days after elimination of oral hygiene procedures. After reinstating plaque control, the gingiva returned to a normal condition within seven days.

Gingivitis is characterized by swelling and redness of the free gingival margin. Bleeding is caused by, for example, toothbrushing and gentle probing by a dentist. There is a loss in the connective tissue tone, which tends to open the gingival sulcus. The disease process may be combatted by either eliminating the plaque or by altering the environment by changing the composition of the plaque.

In order to colonize a surface, bacteria must be able to adhere to the surface in question. The mucous epithelium of the oral cavity is constantly renewed, so that bacteria adhering to the mucosal surface will tend to be sloughed off together with the outer layer of dead cells of the epithelium, thus preventing bacterial invasion of the living tissue underneath the dead epithelial cells. On the other hand, the dental surface constitutes a firm non-living base to which bacteria effectively adhere. The bacterial colonies on the dental surface (plaque), especially at the gingival margin and in the subgingival region, are not removed by any similar process, resulting in an antibacterial immune reaction from the surrounding tissue evident as a chronic inflammation of the gingival tissue. Under normal and healthy conditions this inflammatory reaction is mild, with a delicate balance being struck between colonizing bacteria and antibacterial effect.

Inflammation of the gingiva due to bacterial colonization of the dental surfaces is therefore an important initial stage of periodontitis. If the bacterial colonies (plaque) are not removed, accumulation of bacteria along the gingival margin or in the dento-gingival region will lead to increased gingival inflammation and destruction of the periodontal membrane possibly followed by bone resorption. Eventually a periodontal pocket develops in which more bacteria accumulate, resulting in increased inflammation and infection proper of the tissue so as to lead to a more pronounced degradation of the tooth-supporting tissue.

Wherever there is a plaque coated surface, calcium ions can take part in chemical reactions, giving rise to formation of calculus. Calculus can be found on the tooth surface as supra-gingival or subgingival deposits. These deposits must be removed in order to maintain normal gingival conditions.

A characteristic of periodontal infection is that once bacteria/plaque have established themselves (i.e. infected) firmly in a periodontal pocket, the natural humoral defense mechanisms are not capable of dealing with the infection, and the plaque may turn into hard deposits, i.e. calculus.

Apart from the general inflammation caused by the presence of bacteria/plaque, the release of hydrolytic enzymes like hyaluronidase, desoxyribonuclease, collagenase and protease probably contributes to the destruction of dental tissue.

The severity of tissue damage probably depends on the antigen/antibody reaction of the organism as well as the degree of retention of inflammatory products in the periodontal pockets. Accumulation of mediators of local inflammation accelerates the process. In most cases the process is slow, with immunoinfiltration of the gingival tissue and formation of granulation tissue which contains inflammatory cells. Occasionally, this slow progression is superseded by acute exacerbations with accumulation of inflammatory cells and release of lysosomal enzymes. Such exacerbations are probably due to changes in the bacterial flora.

Juvenile periodontitis differs from the above marginal periodontitis only by an early onset, and by often involving certain groups of teeth and being accompanied by a much lesser degree of plaque formation. It begins in late childhood, resulting in a pronounced loss of the teeth's supporting tissue, and it too is an infectious disease on a par with other periodontal diseases.

Current periodontal therapy is directed towards the removal of bacterial plaque and calculus deposits—subgingival and supragingival plaque. These goals are usually achieved by means of scaling and polishing, instruction in oral hygiene procedures, periodontal surgery where indicated and periodic maintenance.

Another option for treatment which remains to be fully evaluated is the possibility of disrupting the subgingival microflora in such a way that supragingival plaque control becomes less important. One potential approach to such a treatment is intensive intermittent disruption using local or systemic antimicrobial agents, examples of which are metronidazole, tetracycline and erythromycin. Such agents may also be used for irrigation of the periodontal pockets. The potential effect is based on the concept that alteration of the subgingival microflora at appropriate intervals may be sufficient to prevent the development of an ecosystem suitable to the reestablishment of pathogens in adequate levels for disease initiation. Another approach is bacterial substitution, replacing potential pathogens with bacteria which occupy the same ecological niche but have a reduced pathogenic potential.

Still another approach is the use of chemical agents which will alter plaque and subgingival microflora sufficiently to prevent gingivitis or the development of gingivitis into periodontitis.

A vast number of chemical agents have been evaluated as potential antiplaque/antigingivitis agents. The first generation agents are antibacterial agents with limited effectiveness. These agents are effective as antibacterials in vitro, but are either not retained intraorally or they are rapidly released. Therefore, they inhibit the bacteria for a short period of time, after which time bacteria growth is resumed. Their clinical effect is limited unless the agents are used frequently, i.e. four to six times a day. This group includes topical antibiotics, oxygenating compounds, quaternary ammonium compounds, phenolic compounds, and sanguinarine. The second generation agents are effective not only in vitro but also in vivo, due to their retention and release kinetics. At present, chlorhexidine and chlorhexidine analogues are the primary second generation compounds, and stannous fluoride may also qualify as belonging to this group.

Penicillin, tetracycline, erythromycin, polymyxin B, kanamycin, metronidazole and spiromycin have been used for anti-plaque treatment. However, the potential for the development of bacterial resistance and hypersensitivity reactions should limit the use of antibiotics for plaque control purposes. In general, antibiotics may hold great promise for specific bacterial diseases in the oral cavity, but they appear to be inappropriate for the routine control of supragingival plaque and associated diseases.

Quaternary ammonium compounds are cationic surface agents which are capable of reducing surface tension, absorbing to negatively charged surfaces and disrupting membranes. Plaque reducing effects have been reported with benzethonium chloride and cetylpyridinium chloride at 0.1% when used four times daily. Side effects with quaternary ammonium compounds have included both ulcerations and discomfort.

Phenolic compounds have a long history of use in the oral cavity as either a mouthwash or as throat lozenges. A commercial preparation (Listerine®) of thymol, eucalyptol, methyl salicylate, benzoic acid and boric acid has shown a certain plaque reducing effect as compared to a placebo. It is not clear whether the degree of plaque inhibition due to this agent is of long-term value in the prevention of parodontitis.

Sanguinarine, a benzophenanthradine alkaloid, has recently been reported to be potentially useful as a plaque control agent. Preliminary studies indicate that sanguinarine is capable of providing some reduction and prevention of plaque and gingivitis.

Chlorhexidine gluconate in 0.1-0.2% solutions and 1% gels have been shown to exert an effective plaque inhibiting and anti-gingivitis effect, when used short-term. A few long-term studies with chlorhexidine gluconate have also shown promising effects against plaque formation. The oral use of chlorhexidine has been associated with staining of the teeth and tongue and a bitter taste, and longer use often gives rise to alterations of the mucosa. Owing to the cationic nature of the compound, it is difficult to mask the taste by addition of flavoring agents without affecting the biological activity. Other agents such as alexidine and octenidine are structurally similar to chlorhexidine, and appear have a comparable effect.

In summary, treatment of gingivitis and periodontitis has mainly been prophylactic, emphasizing the importance of removing calculus and dental plaque and generally improving oral hygiene by mechanical means such as toothbrushing using fluoride-containing toothpastes etc., and using dental floss, toothpicks and the like. When necessary, surgical methods have been used in order to reduce the depth of the periodontal pockets.

Systemic or topical antibacterial treatment with tetracycline or the like has also been shown to have some effect, especially during acute infectious episodes, and finally, irrigating or rinsing the mouth with antiseptics such as chlorohexidine has been shown to exert a certain, if limited, effect, especially on gingivitis and plaque formation. However, none of these treatments are entirely satisfactory as they either require a high degree of patient compliance and/or do not possess a high degree of efficiency.

SUMMARY OF THE INVENTION

It has surprisingly been found that sulphated saccharides, in particular sucralfate, exert a highly beneficial effect on a variety of dental conditions and diseases when applied topically on teeth or gingiva.

Accordingly, in one aspect, the present invention relates to the use of a sulphated saccharide or a salt or a complex thereof as an ingredient in a topical preparation for the prophylaxis or treatment of diseases or conditions of the tooth or tooth-supporting tissue. In the following, such diseases or conditions are occasionally referred to as dental diseases or conditions.

In contradistinction to the known means of treating or preventing dental conditions, excellent results have been obtained according to the present invention, by using a sulphated saccharide such as sucralfate, in connection with diseases such as gingivitis, periodontitis, alveolitis, and infections such as oral candida.

Sucralfate has previously been indicated for the treatment of gastric and duodenal ulcers (cf. U.S. Pat. No. 3,432,489; EP 161816; EP 192640) and for the treatment of emesis and diarrhoea in dogs and cats (cf. EP 133880). In radiolabelled form, sucralfate has also been used as a diagnostic agent for the imaging of gastrointestinal mucosa since, as mentioned above, the substance binds selectively to ulcerated areas in the stomach and upper small intestine (cf. EP 107209).

*The American Journal of Gastroenterology*, 80(3), 1985, pp. 206-209; "Sucralfate: Nonulcer Uses" suggests the use of sucralfate for a variety of applications apart from the treatment of gastric and duodenal ulcer, including the treatment of chemotherapy induced stomatitis 6 g sucralfate/15 ml glycerol), post-sclerotic ulcer, reflux oesophagitis and bile reflux oesophagitis as well as for counteracting the ulcerogenic effects of aspirin. Also, Ferraro and Mattern, *Drug Intell. Clin. Pharm.* 18, 1984, p. 153, report the use of a sucralfate suspension for treating chemotherapy-induced mouth ulcers (stomatitis), utilizing the ability of sucralfate to adhere to ulcers (vide above). However, the is no indication that sucralfate may be used for other purposes than treating mucosal ulcers. Similarly, EP 136 100 suggests the possible use of a sucralfate suspension for treating ulcers in the mouth but does not indicate any non-ulcer use of the substance.

EP 230 023 describes pharmaceutical compositions comprising sulphated oligosaccharides for wound healing. This disclosure indicates the use of these substances for the enhancement of healing of wounds in collagen containing tissues, including skin and bone. It refers in particular to skin ulcers characterized by breaches or ruptures of the skin barrier. It is stated in the disclosure that polysulphated saccharides are believed to be involved in the stimulation of migration of repair cells, such as fibroblasts, into the wound site, resulting in neovascularization. It is further stated that sucralfate gives rise to inflammatory reactions, and that wound healing with neovascularization and fibroblast (rather than macrophage) migration was not observed with sucralfate. It is also stated that a low level of 0.1 to 1 mg/ml of the polysulphated saccharide is preferred in order to avoid local haemorrage or inflammation at the wound side. In contradiction to this, excellent anti-inflammatory effects have been obtained according to the present invention by using sucralfate topically on the gingiva. The disclosure also mentions that polysulphated saccharides may be used to promote bone healing, and that because of this healing effect they are believed to be suitable for use in or as prosthesic devices, for treatment of periodontal disease and in artificial skin. Periodontal disease in this context would seem to be speculatively listed because of the claimed bone healing effect.

Thus, the above references do not indicate that sucralfate or other polysulphated saccharides exert anti-inflammatory effects, antiplaque effects, or that they stabilize or strengthen cell surfaces and intercellular matrices, including the epithelial and mucosal surfaces. On the contrary, the above mentioned EP 230 023 states that sucralfate actually contributes to inflammation. In view of the results hitherto obtained, which show binding of sucralfate to wounded mucosal surfaces, it is considered surprising that sucralfate, and probably the entire group of polysulphated saccharides, may be used for indications not involving wounded or ulcerated oral mucosa, but rather inflammatory diseases such as gingivitis and periodontitis, and for preventing plaque and calculus formation in the gingival pocket.

It has been observed that one sulphated saccharide, sucralfate, when used internally in the treatment of gastric ulcers, binds preferentially to the surface of the ulcer. It is currently believed that this is a property which is common to sulphated saccharides and that it is the result of an ability of sulphated saccharides to bind to proteoglycans and hyaluronic acid, which are the components of the surface of many cells and protect or stabilize them so that the cell surface remains intact. In other cases, e.g. in connective tissue, including gingiva, hyaluronic acid and proteoglycans form a protective matrix in which cells are embedded. Furthermore, it is known that certain sulphated saccharides, e.g. heparan sulphate, dextran sulphate and xylose sulphate, are hyaluronidase inhibitors. Hyaluronidases are enzymes which catalytically cleave the glycosidic bonds of hyaluronic acid. The decomposition of hyaluronic acid by hyaluronidases therefore leads to exposure of the cells to damage from various agents such as pathogens and inflammatory substances. It has been demonstrated (P. M. Bartold and R. C. Page, *J. Oral Path.* 15, 1986, pp. 367–374; K. S. Last et al., *Archs Oral Biol.* 30 (3), 1985, pp. 275–281) that the presence of degradation products of hyaluronic acid in cervicular fluid present in the periodontal pockets are correlated with clinical signs of periodontitis. Thus, it is assumed that by inhibiting hyaluronidase, sulphated saccharides promote the regeneration of tissue by promoting the regeneration of the layer of matrix containing hyaluronic acid and proteoglycans. Sulphated saccharides such as sucralfate may also modify or inhibit inflammatory reactions and/or stimulate tissue regenerative processes by other not yet fully understood mechanisms.

The non-aluminium complexed form of sucralfate is a salt of sucrose octakis(hydrogen sulphate), which is a very strongly negatively charged entity. It is contemplated that the effects of sucralfate and other sulphated saccharides can in part be ascribed to these strong electrostatic forces. They may be important in preventing pellicle formation on tooth surfaces, and they may also play an important role in the modification and protection of the cell surface. It is believed that a normal or healthy cell surface has a strong electro-negative charge, which is disturbed when the cell surface is impaired. Sucrose octakis(hydrogen sulphate) salts and other sulphated saccharide moieties may act as electro-negative charges which can reestablish the negative surface charge of the "wounded cell area", and thereby exert a cell protecting, wound healing and anti-inflammatory effect.

Vitamin C and sucralfate would seem to be related in several aspects. Chemically, they are both structurally related to glucose and other hexoses. At the tissue level, both compounds are associated with the synthesis of intercellular substances, including collagen, and it is known that vitamin C stimulates the synthesis of sulphated proteoglycans. Depletion of vitamin C leads to scurvy, which is characterized by, among other things, impaired wound healing and gingivitis. In clinical studies it has been possible to demonstrate a close relationship between gingivitis and vitamin C intake. Sucralfate has been demonstrated to enhance wound healing and to improve gingivitis when applied topically. Recently, vitamin C has also been associated with immunoenhancing, anti-inflammatory and anti-allergic effects. The anti-inflammatory effect of vitamin C is, among other things, a result of inhibition of myeloperoxidase and aryl sulphatase activity, and possibly also the elimination of free radicals. It is contemplated that sucralfate may possess the same properties as vitamin C with respect to antioxidant effect and inhibition of myeloperoxidase and other enzymes which play a role in inflammatory processes.

Sucralfate has been shown to have a plaque reducing and modifying effect when used topically in the oral cavity. The mechanisms involved in formation of plaque are still little understood. The adhesive interaction involved in plaque formation appears to be very complex, as may be deduced a prior from the wide variations in the chemical composition of the acquired pellicle and interbacterial matrix. The constituents of saliva, such as high molecular glycoproteins, may play an important role in the removal of bacteria from the mouth by inhibiting bacterial attachment to oral surfaces. These findings (Embery & Sdhogg, *Proc. of a workshop on saliva-dental plaque and enamel surface interactions*, Strasbourg, Ed. R. M. Frank & S. A. Leach, pp. 185–194, October 1981) suggest that saliva, by mimicing the bacterial binding sites on teeth and the epithelial cell surfaces, may competitively inhibit bacterial attachment. It is contemplated that sucralfate, via a modulating/stimulating effect on glucosaminoglycanes and hyaluronic acid either directly or via inhibition/stimulation of various enzymes, enhances the ability of salivary components to mask bacterial binding sites and to induce bacterial aggregation, thereby diminishing or preventing plaque formation, in the gingival sulcus/pocket. Lectin-like interactions also appear of importance in the aggregation and attachment of oral bacteria. It has furthermore been observed that there is a similarity between the GAG (glycosaminoglycans) in mixed dental plaque and calculus and gingival tissues, suggesting that periodontal breakdown may be a factor in the accumulation of GAG in subgingival calculus. Inhibition of GAG breakdown by sucralfate will thus prevent the formation of plaque and calculus. Furthermore, the group of compounds belonging to the glycosaminoglycanes has proved to be a useful model series with which to study the binding properties of hydroxyapatite. The binding of hydroxyapatite is enhanced by calcium ions and inhibited by fluoride, and it is electrostatic in nature. It is therefore not unlikely that modifications of GAG's by sucralfate and other polysulphated saccharides can interfere with initial pellicle formation and the binding of bacteria to the surface of the teeth.

In a further aspect, the present invention relates to a method of preventing or treating dental diseases or conditions, the method comprising topically applying on teeth or tooth-supporting tissue, a prophylactically or therapeutically effective amount of a sulphated saccharide or a salt or a complex thereof.

DETAILED DISCLOSURE OF THE INVENTION

The sulphated saccharide used in accordance with the invention may be a monosaccharide, for instance xylose, fructose or glucose, an oligosaccharide, in particular a disaccharide such as sucrose, lactose, maltose or cellobiose, or a polysaccharide such as dextran, heparan, dermatan, proteodermatan, hyaluronic acid, heparin, chondroitin, amylose, glucosamine, glucosaminoglycan and a mucopolysaccharide or a subunit thereof.

In certain cases, it may be an advantage to use the sulphated saccharide in combination with another wound-healing substance such as a non-sulphated polysaccharide, for instance hyaluronic acid, vide Example 3.

The saccharide is preferably a polysulphated or persulphated saccharide, which means that two or more sulphur-containing moieties may be present as substituents on the carbohydrate moiety.

In some cases, the sulphated saccharide may be complexed with or form a salt with a metal, e.g. an alkali or alkaline earth metal such as Na, K, Ca, Sr, Mg or Ba, or Al, Zn, Cu, Ga, Bi and Mn, or with an organic base. The salts are preferably selected from those which are sparingly soluble in water, in order to obtain a slow release effect when they are used topically in the oral cavity. The currently preferred metal is aluminium, optionally in the form of aluminium hydroxide. In the sulphated saccharide, aluminium complexes with the sulphate moiety. Thus, a preferred class of sulphated saccharides is aluminium disaccharide polysulphates of which the currently most preferred substance is sucralfate.

Sucralfate may be represented by the following formula:

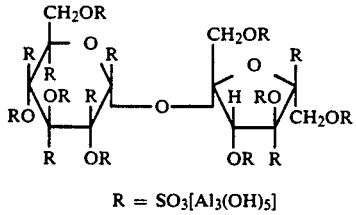

$R = SO_3[Al_3(OH)_5]$

The substance may, for instance, be prepared as disclosed in U.S. Pat. No. 3,432,489 by reacting a 1–10% aqueous solution of a disaccharide polysulphate or an alkali metal or alkaline earth metal salt thereof with a 1–10% aqueous solution containing aluminium ions, preferably $AlCl(OH)_2$ at room temperature and a pH of 4–4.5. The disaccharide polysulphate is prepared by reacting a disaccharide with $ClSO_3H$, $H_2SO_4$ or $H_2SO_4$-$C_5H_5N$.

Sucralfate may also be termed sucrose octakis(hydrogen sulphate) aluminium complex. Its CAS number is 54182-58-0. The commercial product is a white powder which is practically insoluble in water and most organic solvents; it is soluble in acids and alkalis. In practice, there may be slight variations in the chemical composition, for example due to the fact that the sulphation may be slightly incomplete, giving a product that may e.g. contain a certain proportion of molecules which are not octasulphated (persulphated), but which instead are sulphated to a lesser degree, for example heptasulphated. Such minor variations in the commercial product are well known and are reflected in the fact that the aluminium content in commercial products may range from 17 to 21% and the sulphur content from 9.5 to 12.5%. In the present context, the term "sucralfate" also comprises such generally accepted minor variations.

Apart from sulphated saccharides, it is contemplated that other substances may show a similar therepeutic or prophylactic activity in connection with dental diseases and conditions as defined above. Examples of such substances are ketotifen and chromoglycate and other antiallergic agents known to act on and stabilize cell surfaces, such agents also being suspected of inhibiting the activity of hyaluronidase.

Although there may be cases where the sulphated saccharide may be administered as such, it will typically be compounded with one or more pharmaceutically acceptable carriers or excipients to be presented in a form which is suitable for topical application to teeth or tooth-supporting tissue. It will usually be in the form of a fluid, semi-fluid, semi-solid or solid preparation such as a solution, suspension, powder, paste, gel, cream, salve, dental fixative, periodontal implant, chewing gum, chewable tablet, effervescent tablet or lozenge.

The topical preparation may be formulated in accordance with conventional pharmaceutical practice; with pharmaceutical excipients conventionally used for topical applications such as alginate, pectin, gelatin and derivatives thereof, cellulose derivatives such as methyl cellulose, carboxymethyl cellulose or oxidised cellulose, guar gum, acacia gum, karaya gum, tragacanth gum, locust bean gum, bentonite, agar, carbomer, bladderwrack, ceratonia, dextran and derivatives thereof, ghatti gum, hectorite, isphaghula husk, polyvinylpyrrolidone, silica and derivatives thereof, such as silicates, xanthan gum, kaolin, chalk, dicalcium phosphate, alumina, pyrophosphate, talc, starch and derivatives thereof, paraffin, water, vegetable and animal oils, isopropyl myristate, polyethylene, polyethylene oxide, polyethylene glycol and polyethylene glycol esters, polypropylene glycol, glycerol, ethanol, propanol, propylene glycol, glycols, alcohols, fatty alcohols, fixed oils, sodium, potassium, aluminium, magnesium or calcium salts (such as the chloride, carbonate, bicarbonate, citrate, gluconate, lactate, acetate, gluceptate or tartrate), rubbers (artificial or natural) such as chicle, polyisobutylene, etc., sorbitane esters, quaternary ammonium salts, salts of fatty acids and polysorbates.

The preparation of the invention may also contain conventional additives such as thickeners, emulsifiers, anionic, cationic and non-ionic surfactants, stabilizing agents, preservatives, abrasives, flavouring agents, etc.

It has surprisingly been found that a preparation which is particularly effective for prophylactic purposes may be prepared by mixing the sulphated saccharide with a toothpaste preparation. The sulphated saccharide has been found to be compatible with toothpaste preparations of the type commonly available as commercial toothpastes, and can thus be used on a regular basis for the prevention of e.g inflammatory and plaque-related conditions.

A toothpaste will usually contain polishing agents, surfactants, gelling agents and other excipients such as flavouring and colouring agents. The polishing agent may be selected from those which are currently employed for this purpose in dental preparations. Suitable examples are water-insoluble sodium or potassium metaphosphate, hydrated or anhydrous dicalcium phosphate, calcium pyrophosphate, zirconium silicate or mixtures thereof. Particularly useful polishing agents are various forms of silica, especially silica xerogels such as are described in U.S. Pat. No. 3,538,230. The polishing agent is generally finely divided, with a particle size smaller than 10 μm, for example 2-6 μm. The polishing agent may be employed in an amount of 10-99% by weight of the toothpaste. Typically the toothpaste preparations will contain 20-75% of the polishing agent.

A suitable surfactant is normally included in the toothpaste preparations. The surfactant is typically a water-soluble non-soap synthetic organic detergent. Suitable detergents are the water-soluble salts of: higher fatty acid monoglyceride monosulphates (for example sodium hydrogenated coconut fatty acid monoglyceride monosulphate); higher alkyl sulphates (for example sodium lauryl sulphate); alkylarylsulphonates (for example sodium dodecylbenzene-sulphonates); and higher alkyl sulphoacetates (for example sodium lauryl sulphoacetate). In addition, there may be employed saturated higher aliphatic acyl amides of lower aliphatic amino carboxylic acids having 12-16 carbon atoms in the acyl radical and in which the amino acid portion is derived from the lower aliphatic saturated monoaminocarboxylic acids having 2-6 carbon atoms, such as fatty acid amides of glycine, sarcosine alanine 3-aminopropanoic acid and valine, in particular the N-lauryl, myristoyl and palmitoyl sarcosinate compounds. Conventional non-ionic surfactants may also be included if desired.

The surface active materials are generally present in an amount of about 0.05-101%, typically about 0.5-5%, by weight of the toothpaste preparation.

Typically the liquids of the toothpaste will comprise mainly water, glycerol, sorbitol, propylene glycol or mixtures thereof. An advantageous mixture is water and glycerol, preferably with sorbitol. A gelling agent such as natural or synthetic gums and gum-like materials, e.g. Irish Moss or sodium carboxymethylcellulose, may be used. Other gums which may be used are gum tragacanth, polyvinyl-pyrrolidone and starch. They are usually used in an amount up to about 10%, typically about 0.5-5%, by weight of the toothpaste.

The pH of a toothpaste is substantially neutral, such as a pH of about 6-8. If desired, a small amount of a pH-regulating agent, e.g. a small amount of an acid such as citric acid or an alkaline material may be added.

The toothpaste may also contain other materials such as soluble saccharin, flavouring oils (e.g. oils of spearmint, peppermint, wintergreen), colouring or whitening agents (e.g. titanium dioxide), preservatives (e.g. sodium benzoate), emulsifying agents, silicones, alcohol, menthol and chlorophyll compounds (e.g. sodium copper chlorophyllin).

The content of sucralfate or other sulphated saccharide in the toothpaste of the above type or types discussed below will normally be in the range of 1-20% by weight, calculated on the weight of the total toothpaste composition, such as in the range of 5-20% by weight, in particular about 10-20% by weight such as 12-18% by wight. The latter ranges are especially indicated for toothpastes which are used for treatment of gingivitis and periodontosis. It is, however, also interesting to provide toothpastes having a lower content of sucralfate which will often predominantly be adapted for preventive or prophylactic purposes. For such purposes, sucralfate content ranges from about 0.1 to about 5% by weight may be interesting.

A special type of toothpaste are toothpastes which are substantially clear gels. Such toothpastes may either contain no polishing agents at all or may contain the polishing agent in such finely divided form that the gels will still appear substantially clear. Such gel toothpaste types may either be used per se or may be combined with toothpastes containing polishing agents as discussed above.

There are, of course, numerous examples of special toothpastes or dentifrices adapted for special purposes or with special advantages. Thus, e.g., EP 280077 describes a toothpaste which contains stabilized dicalcium phosphate dihydrate, resulting in a high water absorption capacity and an adequate viscosity at low abrasive content; U.S. Pat. No. 4,618,488 discloses stable toothpastes, in particular transparent toothpastes, which contain amourphous silica and/or silicate abrasive with specific surface areas, resulting in long term stability of the transparency of the toothpaste; U.S. Pat. No. 4,632,826 discloses a toothpaste, the polishing agent of which is constituted by a combination of silicagel and/or precipitated silica and weakly calcined alumina mixture, resulting in a toothpaste with low scratching and abrasion effect and with high storage stability; U.S. Pat. No. 4,721,614 discloses a toothpaste which contains sodium bicarbonate as sole abrasive, thus avoiding excessive abrasive properties and retaining a good storage stability; U.S. Pat. No. 4,702,905 and U.S. Pat. No. 4,716, 034 disclose toothpastes which are resistent to syneresis in contact with polyolefin packaging, which toothpastes are thus suitable for packaging in e.g. laminate tubes, mechanical dispensers and flexible sachets; U.S. Pat. No. 4,599,363 discloses a method for wetting and dispersing powders for toothpaste preparations in turbulent liquid medium, the method preventing formation of lumps and loss of powdered solids and resulting in high quality toothpaste compositions; U.S. Pat. No. 4,701,319 discloses a toothpaste which has good stability, viscosity and processing properties, the toothpaste containing abrasive carboxyvinyl polymer, and a carrageenan humectant.

It will be understood that these are only a few examples of toothpaste or dentifrice compositions into which a sulphated saccharide, in particular sucralfate, may be incorporated in the manner described above to obtain the surprising advantages characteristic to the present invention, and that the person skilled in the art would be able to compose any kind of suitable toothpaste or dentifrice composition based on literature references such as the ones given above and the specific information contained herein about suitable manners for incorporating sulphated saccharides in particular sucralfate into such compositions.

The incorporation of sucralfate or other sulphated saccharide in a toothpaste preparation and other dental or oral preparations may be performed in many different ways. Often, it will be preferred to form a suspension of sucralfate and combine the sucralfate suspension with the other preparation ingredients in paste form. Alternatively, dry sucralfate powder may be mixed with the other preparation components, either first with the dry preparation constituents and subsequently with liquid or semi-liquid preparation constituents, or sucralfate powder per se can be incorporated in an otherwise finished preparation.

In this connection it should be mentioned that while the incorporation of sucralfate or other water-insoluble or sparingly water-soluble sulphated saccharides is best performed as described herein taking into consideration the physical and chemical properties of the sulphated saccharide in particular the particle size considerations mentioned below, the incorporation of water-soluble sulphated saccharides, such as sodium and potassium salts of sucrose oktakis (hydrogen sulphate) in toothpastes or dentifrices or other preparations discussed herein will normally be extremely simple and will ordinarily consist in the addition of the sulphated saccharide to the preparation or to constituents thereof in either dry or dissolved form.

For certain purposes, such as "pocket filling materials", denture fixatives and other preparations which are to stay for prolonged periods in contact with wounded or infected areas, the preparation is advantageously one which is capable of adhering to the gingiva, periodontal sulcus/pocket, tooth enamel, dentine, root cement or tooth-supporting tissue on which it is applied, in order to ensure a sufficiently intimate contact between the active substance and the surface in question for a sufficient period of time to obtain an efficient localized action of the sulphated saccharide. Such adhesive properties may be obtained by for example incorporating suitable high molecular weight materials such as pectin, gelatine and methylcellulose into the preparation, preferably together with a non-aqueous liquid vehicle such as a medium chain triglyceride, e.g. a triglyceride comprising acid moieties of a length of about 12-18 carbon atoms.

The preparation may further be one which is biodegradable, meaning that it is capable of being degraded in the body outside the digestive tract. The biodegradable material present in the preparation is one which gives rise to degradation products which are readily eliminated from the body by being metabolized at the cellular level or by disintegrating into smaller components which are eliminated via the kidneys or metabolized in the liver etc. Examples of useful biodegradable materials are synthetic polymers such as polyglycolic acid, polyacetic acid, polylactic acid or copolymers thereof, polycarbonates, polyacetals, polyketals, polyorthoesters, etc., as well as natural polymers such as proteins, e.g. gelatin and collagen, or polysaccharides, e.g. dextran, agarose, pectin, starch, alginates, hyaluronic acid, etc. The biodegradability of the preparation is considered to be particularly advantageous when the preparation is in the form of a periodontal implant, as this would obviate the necessity of surgically removing the implant after the treatment is completed.

Periodontal implants may be prepared by moulding, pressing, extruding, etc. in a manner known per se and subsequently formed into any desired shape such as a film, thread, strip, wedge or sponge. Preparations for insertion into periodontal pockets are, however, preferably in the form of a paste or gel, a suitable quantity of which is introduced into the pocket by means of a suitable instrument such as a syringe.

A chewing gum may be prepared by incorporating the sulphated saccharide into a conventional chewing gum base containing chicle or a synthetic rubber. Similarly, chewable tablets may be prepared by compounding the sulphated saccharide with one or more conventional excipients such as sorbitol, xanthan gum, etc.

The pharmacologically active element in sucralfate is probably the non-aluminium complexed sodium and/or potassium salt of sucrose octakis(hydrogen sulphate). Since such a salt is soluble in water, it would seem that a small particle size would be an important factor when preparing formulations of the sparingly soluble sucralfate. One way of achieving a small sucralfate particle size is by means of milling, grinding or disintegrating apparatus, e.g. a three roll mill, where the sucralfate powder is ground, preferably together with a suitable liquid vehicle having a viscosity adapted to effectively suspend the resulting fine particles, and preferably a relatively low vapour pressure so that no excessive evaporation with resulting agglomeration of the fine particles will occur, such as a polyalcohol, for example glycerin or polyethylene glycol. The resulting preparation will normally contain up to 60-70% by weight of sucralfate particles with a fairly uniform particle size of about 5-10 $\mu$m or less (for 95% by weight of the sucralfate), the particles being substantially evenly suspended in the vehicle. Such a paste can then be further suspended in any suitable pharmaceutical preparation using well known pharmaceutical methods. Another starting point for a small particle size sucralfate formulation is sucralfate "filter cake", which is sucralfate containing about 50% by weight of water, and with a particle size of about 5-10 $\mu$m or less. This material can be mixed with, for instance, a water-miscible liquid which has a relatively low vapour pressure, such as glycerin, in order to prevent the water from evaporating, and the sucralfate particles will retain their small size. Another important factor to take into consideration when preparing formulations of sucralfate and other sulphated saccharides is the strong negative charge of salts of sucrose octakis(hydrogen sulphate), and probably of most sulphated saccharides. The pharmacological effect of sucralfate, salts of sucrose octakis(hydrogen sulphate) and other sulphated saccharides probably depends on this negatively charged entity, and the pharmacological effect of the drug may be reduced by the presence of positively charged mono- and divalent ions in the vehicle.

The topical preparation to be used for the present purpose generally comprises the sulphated saccharide in an amount of 0.001-99%, typically 0.01-75%, more typically 0.1-20%, especially 1-10% by weight of the total preparation. In particular, when the sulphated saccharide is sucralfate, a preferred concentration thereof in the preparation is often from 0.5-50%, especially 0.5-25%, especially 1-5%, such as 1-10%. It is suitably applied 1-10 times a day, dependent on the type and severity of the condition to be treated. Preparations for application in periodontal pockets, however, are preferably applied at regular intervals during the entire treatment period.

The preparation may contain other active agents than the sulphated saccharide, such as antibiotics, antibacterial or antimicrobial agents, antiviral agents, antimycotic agents, bacteriostatic agents (e.g. sulphonamides), antiseptic agents, disinfectants, local anesthetics or analgesics, antiinflammatory agents, antineoplastic agents and anticaries agents (e.g. fluoride).

As mentioned above, the sulphated saccharide is indicated for use in connection with any dental disease or condition initially involving bacterial colonization, inflammation and/or infection of the teeth or tooth-supporting tissue. The sulphated saccharide may thus be used for treating or preventing dental caries, dental plaque or calculus, gingivitis, periodontitis, alveolitis, pulpitis and osteomyelitis. It has further been shown that the sulphated saccharide may be useful for preventing post-extractive, post-surgical or post-traumatic wounds or bone resorption, prosthetic irritation, irritation, inflammation or infection associated with tooth eruption or extraction, cysts and neoplastic conditions originating in the tooth-supporting tissue, and bacterial, mycotic and viral oral infections, and it has been shown to be effective in the treatment of oral infections such as candida.

The invention is further illustrated by the following non-limiting examples.

EXAMPLE 1

A topical paste preparation for insertions into periodontal pockets and as fixative for dentures was prepared from the following ingredients:

| | |
|---|---|
| Sucralfate * | 30 g |
| Pectin | 10 g |
| Gelatin | 10 g |
| Carboxymethylcellulose | 10 g |
| Medium-chain triglycerides | 60 g |

* Provided by Abic Laboratories, Israel, in finely divided form (particle size: 95% by weight <250 μm).

The finely divided sucralfate was thoroughly mixed with the other ingredients in finely divided form. The medium-chain triglycerides were added to the resulting powder to a suitable paste-like consistency and a substantially homogeneous dispersion of the particulate components.

EXAMPLE 2

A topical paste preparation for insertion into periodontal pockets and as fixative for dentures was prepared from the following ingredients:

| | |
|---|---|
| Sucralfate * | 10 g |
| Gelatin | 10 g |
| Pectin | 10 g |
| Medium-chain triglycerides | 15 g |
| Hydrogenated coconut oil | 15 g |

* Provided by Farmos Pharmaceutical, Finland, 95% by weight <250 μm.

The finely-divided sucralfate was thoroughly mixed with the pectin and gelatine in finely divided form. The medium-chain triglycerides and hydrogenated coconut oil were added to the resulting powder to a suitable paste-like consistency and a substantially homogeneous dispersion of the particulate components.

EXAMPLE 3

A topical paste preparation for insertion into infected periodontal pockets was prepared from the following ingredients:

| | |
|---|---|
| Sucralfate * | 30 g |
| Tetracycline | 3 g |
| Hyaluronic acid ** | 0.3 g |
| Pectin | 10 g |
| Gelatin | 10 g |
| CMC | 10 g |
| Medium-chain triglycerides | 60 g |

* Provided by Farmos Pharmaceutical, Finland, 95% by weight <250 μm.
** Obtained from human umbilical cord (Sigma)

The finely divided sucralfate was thoroughly mixed with other ingredients in finely divided form. The medium-chain triglycerides were added to the resulting powder to a suitable consistency and a substantially homogeneous dispersion of the particulate components.

EXAMPLE 4

A topical gel preparation was prepared by mixing 15 g of sucralfate powder supplemented by Guilini Chemie, West Germany, 95% by weight <250 μm) with 15 ml of 3% HCl. The mixture formed a translucent adhesive gel.

EXAMPLE 5

A topical gel preparation was made by melting 50 g of gelatine and mixing into it 20 g of the same sucralfate powder as in Example 4.

EXAMPLE 6

A toothpaste preparation was prepared by mixing 15 g of the same sucralfate powder as used in Example 4 with 15 ml of glycerol and adjusting the paste to the desired consistency by adding glycerol after 2 days.

EXAMPLE 7

A toothpaste preparation was prepared by mixing 10 g of sucralfate (provided by Guilini Chemie, W. Germany, 95% by weight <250 μm) powder with 12 ml of water. This mixture was subsequently mixed with 12 g of a toothpaste containing polishing agent (Colgate "Blue Mint").

EXAMPLE 8

A toothpaste preparation was made by mixing 10 g of sucralfate powder with 70 g of a base prepared in advance and comprising:

| | |
|---|---|
| Sodium monofluorphosphate | .38 % |
| Sodium fluoride | 0.11 % |
| Sorbitol (70% sol) | 58 % |
| Silicon dioxide | 18 % |
| Glycerine (98%) | 10.1 % |
| Polyethylene glycol (PEG 600) | 3 % |
| Sodium lauryl phosphat | 1.3 % |
| Sodium saccharine | 0.3 % |
| Dicalcium phosphat | 0.1 % |
| Titanium dioxide | 0.01 % |
| Tixocil | 4 % |
| Flavour | 0.7 % | and adjusting the consistency by adding distilled water.

EXAMPLE 9

A toothpaste was prepared by mixing:

| | |
|---|---|
| Aluminium abrasive | 35 % |
| Sterile water | 29.3 % |
| Glycerine | 22 % |
| Sucralfate * | 10 % |
| Hydroxyethylcellulose (Natrosol 250 M) | 1.4 % |
| Polyethylene glycol 40 di-isostearat | 1 % |
| Flavour K91-4037 | 1 % |
| Sodium saccharine | 0.4 % |

* Micronized sucralfate (10 μm) provided by Guilini Chemie, W. Germany

EXAMPLE 10

A chewing gum was prepared by heating a commercial chewing gum to 100° C. and then stirring 10% by weight of sucralfate powder into the melted gum base. The gum base had the following composition:

| | |
|---|---|
| Hydrogen peroxide (solid) | 5 mg |
| Sorbitol | 285 mg |
| Mannitol | 7 mg |
| Saccharin | 0.7 mg |

Another sucralfate chewing gum was prepared in the same manner using a gum based on chicle, sorbitol, dicalcium phosphate and saccharine.

EXAMPLE 11

Clinical trials

A) A paste according to Example 3 was used for treating 10 cases of periodontitis accompanied by 5-10 mm deep, infected (i.e. containing pus) periodontal pockets by introducing the paste into pockets by means of a spatula, after scaling the calculus from the root surface. The paste was left in the pockets for a week, after which the treatment was repeated.

On examination 2 days after the initial treatment there was no longer any pus or inflammation of the gingiva and the patients did not complain of any pain or irritation. The depth of the periodontal pockets was observed to be reduced. After 2 weeks it was observed that the mobile teeth had become more firmly fixed into the alveole and there were no clinical signs of inflammation.

It was concluded that this paste preparation is suitable for treating periodontic disease accompanied by infected periodontal pockets and loosening of the affected teeth. The sticky paste prevents the infection of the cleaned pocket.

B) A paste according to Example 1 was used substantially as described under A) with the exception that the treated periodontal pockets were not infected, as determined by the absence of pus. As in A), the number of treated patients was 10.

After a few days the clinical signs of inflammation, bleeding and oedema had disappeared, the depth of periodontal pockets had been reduced, the treated teeth had become immobile, and none of the patients had experienced clinical side effects of the treatment. 2 weeks later, the depths of the periodontal pockets had been further reduced.

It is therefore concluded that the paste according to Example 1 is well-suited for treating periodontal pockets, the more so as the patient' gingiva were no longer painful, so that they could resume brushing their teeth and otherwise maintaining a normal oral hygienic standard.

C) The preparation of Example 2 was used for treating 24 cases of periodontitis in which the patients had periodontal pockets of a depth of up to 5-6 mm. After depuration and cleaning the teeth, the gel was injected into the periodontal pockets by means of a syringe provided with a blunt needle.

When examined 2 days later, the patients had not experienced any pain after the treatment, and the inflammation of the gingiva was reduced to an extent normally observed only after a weeks treatment.

D) A toothpaste as described in Example 6 was used in the treatment of 100 cases of gingivitis by carefully applying, both with and without initial prophylactic polishing and scaling, the paste on the gingival margin for about 2 minutes using a soft bristled toothbrush. This treatment was repeated two or more times daily for several weeks (maximum treatment period 6 months).

On examination after a few days an almost healthy gingival mucosa was observed, and 50 of the patients who used the toothpaste for longer periods up to six months showed none of the discolorations of the teeth and of the tongue associated with the use of chlorohexidine and antibiotics.

E) A toothpaste according to Example 7 and Example 9 were used by 150 patients (75 patients for each toothpaste) constantly or intermittently for periods of from 3 to 12 months (median 6 months), as a sole treatment for gingivitis. The toothpastes were used morning and evening, the gingival margin being brushed horizontally with a soft bristled toothbrush. The patients were instructed to not rinse their mouth until one minute after brushing. As a sole treatment, this resulted in healthy gingiva with no bleeding and swelling, and a remarkable reduction in subgigival deposits of plaque and calculus has been shown, resulting in a firm binding of the gingiva margin, and thereby effectively preventing further progression of periodontic disease.

F) Another 50 patients used the toothpaste of Example 9, but containing only 2% sucralfate instead of 12% sucralfate. The patient category and the use of the toothpaste were identical with the above-mentioned Example 11 E), and the anti-gingivitis effect was the same, indicating that even a low concentration of 2% sucralfate in a dentifrice would seem to be sufficient as a gingivitis-preventing treatment.

G) Pastes according to Example 1 and Example 2 were used as a denture fixative. Twenty patients with difficult upper dentures used the pastes for periods of up to one year. The pastes have resulted in a good fixation of the dentures and have had the additional advantages of being tasteless, providing a long-lasting (up to 12 hours) gluing effect and functioning as a kind of shock absorbing paste, with very little irritation of the gums and mucosa. The pastes have also been used as glue in immediate dentures (immediately after extraction of teeth), and have given rise to a very quick healing of the gums.

H) The paste of Example 2 and the gel of Example 4 have been used in about 20 cases of third lower molar eruptions, applying them under the mucosal flap. They have resulted in a good anti-inflammatory effect equivalent to the effect seen following the use of chlorohexidine and antibiotics such as Nebaticine.

I) The paste of Example 2 has been used in 25 cases of third lower molar extractions, placed on a gauze mesh, and there has been no incidence of dry sockets alveolitis.

J) The gel of Example 5 was filled into impression-type syringes. Before use, the syringes were heated to 70° C. in a water-bath, the gel being used to fill out periodontal pockets. About 10 patients have been treated, and the effect has been good, with a marked anti-inflammatory effect and the pocket being well protected from contamination.

K) The gel preparation of example 4 was used in the gingival margin and left for 1-2 days, in 50 patients with severe gingivitis with swelling and bleeding, the patients thus being unable to maintain proper oral hygiene. They were instructed not to brush their teeth. Inspection after one day showed a remarkable healing of the gingivitis, making it possible to institute the relevant dental treatment without discomfort. The gel acquires a rubber-like consistency and can thus easily be removed when necessary.

L) The gel of Example 4 has also been used on dentures as a fixative, and it has in a few cases been applied topically on the infected area in the treatment of oral candida infections. It has also been used following minor surgery in the oral cavity in about 20 cases, being applied on the wound area and providing pain relief and an anti-inflammatory and wound healing effect.

EXAMPLE 12

For the curative management of patients with deep periodontal pockets (more than about 5 mm), which constitute about 20% of all periodontosis cases, it is probably necessary to have a method of treatment which can remove the subgingival bacterial plaque formation and keep the dental surface free of new plaque formation for a period of time which is sufficiently long to allow the gingival tissue to normalize and the contact epithelium to be re-created and attach to the tooth. For that purpose, a special cleaning system, based on a modified ultra-sonic Odontoson (3 N Special, Lennart Goof A/S, Usserod Molle. 2900 Horsholm, Denmark), has been developed. The apparatus is modified by placing a water jet-pipe nearly parallel with the ultrasonic needle, in such a way that the water jet stream is directed alongside the ultrasonic needle, hitting the point of the needle. With this construction, it is possible to direct both the ultrasonic needle and the water jet stream into the periodontal pocket simultaneously. The combined effect of the ultrasonic needle being carefully moved over the surface of the pocket and the tooth surface while the water vigorously hits the tip of the needle has shown to be very effective in removing bacterial plaque from the surface of the teeth. The amount of water needed is approximately 30-50 ml per minute. The cleaning effect is significantly improved by adding sucralfate in a concentration of approximately 0.1-1% by weight to the flushing water. The addition of sucralfate also significantly delays the formation of new bacterial plaque, and it is helpful in guiding the dentist when removing the subgingival plaque, in that the water stops foaming when the plaque is completely removed.

Six patients with advanced periodontitis and periondontal pockets of a depth of 8-12 mm were treated with the above mentioned cleaning system. Sucralfate 0.1% by weight, in the form of Antepsin Granulate, Farmos, was added to the flushing water. This treatment was repeated at appropriate intervals for up to 4 weeks. In all six cases there was a nearly complete healing of the periodontotic conditions. Another six patients with the same grade of parodontitis underwent the same cleaning of the periodontal pockets followed by injection of a sucralfate paste (Example 2) using a syringe with a blunt needle. After 7 to 14 days, the deep periodontal pockets had nearly disappeared and the patients were classified as being greatly improved with respect to periodontitis. Inflammatory signs and symptoms had completely disappeared and at a follow up after 4 months, there were no signs of reappearance of periodontitis.

EXAMPLE 13

Sucralfate has been shown to be highly effective as an anti-inflammatory agent and moderately effective as a plaque reducing agent when used as a mouthwash.

In a study comprising 13 adults (aged 19-46 years) a 2% by weight aqueous suspension of sucralfate was used 2-3 times daily as a mouthwash for a period of 12 days. No other oral hygiene was allowed during this test period of 12 days. No other oral hygiene was allowed during this test period. Before the start of the study, the participants' teeth were polished and it was controlled that none of the participants had severe gingivitis or calculus. The test persons received 200 ml of mouthwash flavored with peppermint, and were instructed to rinse the mouth with 10 ml 2-3 times a day. At the start of the study and after 8 and 12 days, plaque control was made with Diaplak, and gingival bleeding was controlled using a periodontal probe to investigate the orifice of the gingival crevice. None of the test persons felt any discomfort during the test period, and none experienced foetor ex ore. The results below summarize measurements of the gingival index (Lee, 1967, *J. Periodont.* 38: 38-44), and plaque index assessed according to the method of Bay & Ainemo.

The mean plaque index before start and before polishing was 0.69, and 1.17, respectively, indicating a very minor increase in dental plaque score during the test period. The condition of the gingivae after 12 days of sucralfate mouthwash as the only means of oral hygiene was perfect, with no signs of beginning inflammatory changes, and the gingival score was 0 for all 13 test persons. Those persons who smoked developed discoloration of the teeth, but apart form this discoloration there were no side effects.

From previous experience it is known that withdrawal of all mechanical oral hygiene procedures in individuals with healthy gingivae for a period of 2-4 weeks will result in clinically detectable gingivitis. On this basis, it can be concluded that topical administration of sucralfate in the mouth exerts a beneficial effect, in that sucralfate is capable of effectively preventing the development of gingivitis.

EXAMPLE 14

Double-blind randomized comparison of a sucralfate dentifrice against a chlorhexidine dentifrice (active control), and a blue minty gel dentifrice (passive control), in adults with mild gingivitis.

The objective of this study was to compare the effect of a 10% sucralfate dentifrice (Example 9) on established gingivitis and plaque with a blue minty gel (negative control), and Corsodoyl ® Gel dentifrice (positive control, 10% chlorhexidine). The subjects were selected from patients attending a general dental practice. Forty-eight (48) subjects meeting the inclusion criteria were randomly allocated to one of the three groups. The subjects were instructed to use only the allocated dentifrice and toothbrush (Oral B ® 35), using enough toothpaste to cover the head of the brush and to brush for one minute morning and night, and to use no other oral hygienic procedures. The subjects received no prophylaxis before the start of the trial.

Scoring system

The following 6 teeth were scored: 6+, 2+, +4, 4−, −2, −6. Swelling was scored at the gingival papilla meseally to the teeth. The gingival index (GI) was scored from 0-3 using the Quikly-Hein GI index, and the plaque index (PI) was scored from 0-5. Pockets were measured by probing. For each tooth, probing was carried out using 3 scores buccaly (distally, midale and meseally) and one score orally (midale). Plaque was scored using the Lambster modification of the Quigley-Hein plaque index after disclosing the teeth with Diaplak (erythrosine). The figures shown below are the sum of all 24 measurements for each index.

The above-described procedure was used at week three (3) and at week six (6) examinations.

Results

Baseline scores obtained at the first visit for swelling, gingivitis, plaque and pocket depths showed that all 48 patients had slight inflammatory changes and mild gingivitis.

At each of the three week and at the six week examinations, the effect of the test dentifrices was evaluated on 37 patients. The effect on gingivitis and plaque formation, respectively, is expressed as the change in the gingival index (GI) and the plaque index (PI) (calculated as post/pre ×100) during the test period. The effect obtained over the first three week period is calculated for patients attending the three week visit, and correspondingly, the effect for the six week period is calculated for patients attending the six week visit. Tables 1 and 2 give the mean values for the three groups.

TABLE 1

| | Mean gingival index (GI) | | |
|---|---|---|---|
| | Placebo | Chlorhexidine | Sucralfate |
| 0-3 weeks: | 109% | 101% | 88% |
| 0-6 weeks: | 110% | 100% | 90% |

TABLE 2

| | Mean plaque index (PI) | | |
|---|---|---|---|
| | Placebo | Chlorhexidine | Sucralfate |
| 0-3 weeks: | 91% | 71% | 83% |
| 0-6 weeks: | 94% | 84% | 92% |

The acceptability and effect of the toothpaste was evaluated by asking the patients at the three week visit about taste, staining of the teeth and tendency to gingival bleeding while brushing. The results are shown in Table 3.

TABLE 3

| Ratings for taste, staining and bleeding | | | | |
|---|---|---|---|---|
| | | Number of patients | | |
| | | Placebo | Chlorhexidine | sucralfate |
| Taste: | Good | 9 | 0 | 6 |
| | Average | 6 | 2 | 4 |
| | Bad | 0 | 10 | 0 |
| Staining: | Less | 0 | 1 | 2 |
| | No change | 13 | 2 | 8 |
| | More | 2 | 9 | 0 |
| Bleeding: | Less | 3 | 1 | 4 |
| | No change | 11 | 11 | 6 |
| | More | 1 | 0 | 0 |

TABLE 3-continued

Conclusion

Chlorhexidine had some effect on plaque formation, and at the three week visit the plaque index for chlorhexidine was reduced to 71% of the baseline findings. Chlorhexidine gave no reduction in the gingival index. The sucralfate dentifrice showed a moderate but consistent beneficial effect on the gingivae. During the first three weeks of the test period the gingival index with sucralfate was reduced from a mean of 1.23 to a mean of 1.08, indicting that most of the bleeding sites had disappeared. There was also some effect of sucralfate on plaque formation.

The sucralfate dentifrice was generally very well accepted. It was rated as having a good taste and was reported by some of the test persons to give less bleeding. Nearly all of the patients were positive with respect to continued use of the sucralfate dentifrice. A few patients reported spontaneously that the sucralfate dentifrice had a beneficial effect on tobacco strains.

Chlorohexidine was nearly unanimously rated as having a bad taste and giving rise to discolouring of the teeth, leading to four out of sixteen test persons using chlorhexidine dropping the test. With few exceptions, the subjects using chlorhexidine would not continue using this test dentifrice.

We claim:

1. A method of preventing, diminishing or treating dental disease in a human, which comprises topically administering into the oral cavity a salve, paste, gel or cream preparation comprising a prophylactically or therapeutically effective amount of an aluminum salt or complex of a sulfated saccharide, said preparation being suitable for dental use.

2. The method of claim 1, wherein the saccharide is an oligosaccharide.

3. The method of claim 2, wherein the oligosaccharide is selected from the group consisting of sucrose, lactose, maltose, and cellobiose.

4. The method of claim 1, wherein the saccharide is polysulphated.

5. The method of claim 4, wherein the saccharide is persulfated.

6. The method of claim 1, wherein the aluminum is in the form of aluminum hydroxide.

7. A method of claim 1, wherein the sulphated saccharide is an aluminum disaccharide polysulphate.

8. The method of claim 7, wherein the sulphated saccharide is sucralfate.

9. The method of claim 1, wherein the sulphated saccharide is formulated as a topical preparation.

10. The method of claim 9, wherein the topical preparation additionally contains a non-sulphated polysaccharide.

11. The method of claim 9, wherein the preparation comprises an adhesive which is capable of adhering to the teeth or tooth-supporting tissue.

12. The method of claim 9, wherein the topical preparation is biodegradable.

13. The method of claim 1, wherein the disease is selected from the group consisting of dental caries, dental plaque, gingivitis, periodontitis, alveolitis, pulpitis, osteomyelitis, post-extractive or post-surgical wounds, tooth eruption, bone resorption, prosthetic irritation, cysts or neoplasms originating is the tooth-supporting tissue, and bacterial, mycotic, and viral oral infections.

14. The method of claim 9, wherein the topical preparation has a form selected from the group consisting of a salve, a paste, a gel, a cream.

15. The method of claim 9, wherein the topical preparation is administered together with one or more other active agents selected from the group consisting of an antibiotic, and antibacterial or antimicrobial agent, an antiviral agent, an antimycotic agent, a bacteriostatic agent, an antiseptic agent, a disinfectant, a local anesthetic or analgesic, an anti-inflammatory agent, an antineoplastic agent, and an anticarious agent.

16. The method of claim 10 wherein the non-sulfated polysaccharide is hyaluronic acid.

17. The method of claim 1 wherein the concentration of sulfated saccharide in the preparation is at least about 1% by weight of the preparation.

18. The method of claim 9 wherein the preparation contains a high molecular weight material selected from the group consisting of pectin, gelatine and methylcellulose, and a triglyceride comprising acid moieties of a length of 14-18 carbon atoms.

19. The method of claim 1 in which the preparation is a dental paste.

20. A topical salve, paste, gel or cream preparation useful in preventing or treating dental disease in a human which comprises a prophylactically or therapeutically effective amount of an aluminum salt or complex of a sulfated saccharide, said preparation being suitable for dental use.

21. The preparation of claim 20, which additionally contains a pharmaceutical excipient.

22. The preparation of claim 20, wherein the saccharide is an oligosaccharide.

23. The preparation of claim 20, wherein the oligosaccharide is selected from the group consisting of sucrose, lactose, maltose and cellobiose.

24. The preparation of claim 20, wherein the saccharide is polysulphated.

25. The preparation of claim 24, wherein the saccharide is persulfated.

26. The preparation of claim 20, wherein the aluminum is in the form of aluminum hydroxide.

27. The preparation of claim 20, wherein the sulphated saccharide is an aluminum disaccharide polysulphate.

28. The preparation of claim 27, wherein the sulphated saccharide is sucralfate.

29. A preparation of claim 20, wherein the topical preparation additionally contains a non-sulphated polysaccharide.

30. The preparation of claim 20, wherein the preparation comprises an adhesive which is capable of adhering to the teeth or tooth-supporting tissue.

31. The preparation of claim 20, wherein the topical preparation is biodegradable.

32. The preparation of claim 20, wherein the disease is selected from the group consisting of dental caries, dental plaque, gingivitis, periodontitis, alveolitis, pulpitis, osteomyelitis, post-extractive or post-surgical wounds, tooth eruption, bone resorption, prosthetic irritation, cysts or neoplasms originating in the tooth-supporting tissue, and bacterial, mycotic, and viral oral infections.

33. The preparation of claim 20, wherein the topical preparation has a form selected from the group consisting of a salve, a paste, a gel, a cream.

34. The preparation of claim 20, wherein the concentration of sulphated saccharide is from about 0.01 to about 75% by weight of the preparation.

35. The preparation of claim 29 wherein the non-sulfated polysaccharide is hyaluronic acid.

36. The preparation of claim 20 wherein the concentration of sulfated saccharide in the preparation is at least about 1% by weight of the preparation.

37. The preparation of claim 20 which contains a high molecular weight material selected from the group consisting of pectin, gelatine and methyl-cellulose, and a triglyceride comprising acid moieties of a length of 12-18 carbon atoms.

38. The preparation of claim 20 which is further characterized as a dental paste.

39. A method of inhibiting the formation of dental plaque which comprises introducing into the oral cavity of a patient a preparation comprising a prophylactically effective amount of a sulfated saccharide, or a salt or complex thereof, said preparation being suitable for dental use.

40. The method of claim 39 wherein the saccharide is an oligosaccharide.

41. The method of claim 39 wherein the preparation comprises a prophylactically effective amount of an aluminum salt or complex of a sulfate saccharide.

42. The method of claim 41 wherein the preparation comprises a prophylactically effective amount of sucralfate.

43. The method of claim 39 wherein the preparation is a dental salve, paste, gel or cream.

44. The method of claim 39 wherein the concentration of sulfated saccharide in the preparation comprises at least about 1% by weight of the preparation.

45. The method of claim 39 wherein the preparation further comprises an adhesive and is applied to and adheres to the gingiva, periodontal sulcus/pocket, tooth enamel, dentine, root cement or tooth-supporting tissue.

46. The method of claim 45 wherein the preparation is biodegradable.

47. The method of claim 1 wherein the dental disease is gingivitis.

48. A toothpaste useful in preventing or treating dental disease in a human which comprises a therapeutically effective amount of sucralfate, which is from about 0.1 to about 20% by weight, solubilized in about 0.05 to about 10% by weight of a water-soluble non-soap synthetic organic detergent preparation.

* * * * *